(12) United States Patent
Bonda et al.

(10) Patent No.: US 8,329,148 B1
(45) Date of Patent: Dec. 11, 2012

(54) PHOTOSTABILIZATION OF COENZYME Q COMPOUNDS WITH ALKOXYCRYLENE COMPOUNDS

(75) Inventors: Craig A. Bonda, Winfield, IL (US); Anna Pavlovic, Elmwood Park, IL (US); Jean Zhang, Hickory Hills, IL (US)

(73) Assignee: Hallstar Innovations Corp., Chicago, IL (US)

( * ) Notice: Subject to any disclaimer, the term of this patent is extended or adjusted under 35 U.S.C. 154(b) by 0 days.

(21) Appl. No.: 13/572,165

(22) Filed: Aug. 10, 2012

Related U.S. Application Data (60) Division of application No. 13/294,339, filed on Nov. 11, 2011, now Pat. No. 8,257,687, which is a continuation-in-part of application No. 13/282,667, filed on Oct. 27, 2011, now Pat. No. 8,278,332, which is a division of application No. 12/533,598, filed on Jul. 31, 2009, now Pat. No. 8,070,989, which is a continuation-in-part of application No. 12/022,758, filed on Jan. 30, 2008, now Pat. No. 7,588,702, which is a continuation-in-part of application No. 11/891,281, filed on Aug. 9, 2007, now Pat. No. 7,597,825.

(51) Int. Cl.
- *A61K 8/00* (2006.01)
- *A61K 8/18* (2006.01)
- *A61Q 17/04* (2006.01)
- *A61K 38/43* (2006.01)

(52) U.S. Cl. ........... 424/59; 252/589; 424/60; 424/94.1; 424/401; 514/690

(58) Field of Classification Search .................. 252/589; 424/59, 60, 94.1, 401; 514/690
See application file for complete search history.

(56) References Cited

U.S. PATENT DOCUMENTS

| | | |
|---|---|---|
| 2,623,060 A | 12/1952 | Cragoe |
| 3,215,724 A | 11/1965 | Strobel et al. |
| 3,337,357 A | 8/1967 | Strobel et al. |
| 4,284,621 A | 8/1981 | Preuss et al. |
| 4,293,542 A | 10/1981 | Lang et al. |
| 4,307,240 A | 12/1981 | Ching |
| 4,396,240 A | 8/1983 | Henson |
| 4,562,278 A | 12/1985 | Hill |
| 4,617,374 A | 10/1986 | Pruett et al. |
| 4,707,537 A | 11/1987 | Pruett et al. |
| 5,576,354 A | 11/1996 | Deflandre et al. |
| 5,663,213 A | 9/1997 | Jones et al. |
| 5,738,842 A | 4/1998 | Raspanti et al. |
| 5,783,307 A | 7/1998 | Fagerburg et al. |
| 5,989,528 A | 11/1999 | Tanner et al. |
| 5,993,789 A | 11/1999 | Bonda et al. |
| 6,113,931 A | 9/2000 | Bonda et al. |
| 6,225,052 B1 | 5/2001 | Batz et al. |
| 6,284,916 B1 | 9/2001 | Bonda et al. |
| 6,485,713 B1 | 11/2002 | Bonda et al. |
| 6,518,451 B2 | 2/2003 | Bonda et al. |
| 6,537,529 B1 | 3/2003 | Bonda |
| 6,551,605 B2 | 4/2003 | Bonda |
| 6,800,274 B2 | 10/2004 | Bonda et al. |
| 6,890,521 B2 | 5/2005 | Bonda |
| 6,905,525 B2 | 6/2005 | Wood et al. |
| 6,919,473 B2 | 7/2005 | Bonda et al. |
| 6,962,692 B2 | 11/2005 | Bonda et al. |
| 7,064,114 B2 | 6/2006 | Yiv et al. |
| 7,201,893 B2 | 4/2007 | Wendel et al. |
| 7,235,587 B2 | 6/2007 | Bonda et al. |
| 7,292,156 B2 | 11/2007 | Smith et al. |
| 7,449,698 B2 | 11/2008 | Nguyen et al. |
| 7,534,420 B2 | 5/2009 | Bonda et al. |
| 7,588,702 B2 | 9/2009 | Bonda et al. |
| 7,597,825 B2 | 10/2009 | Bonda et al. |
| 2002/0127192 A1 | 9/2002 | Murphy et al. |
| 2003/0000130 A1 | 1/2003 | Wood et al. |

(Continued)

FOREIGN PATENT DOCUMENTS

DE 1222926 8/1966

(Continued)

OTHER PUBLICATIONS

"Amoco® NDC for Coatings, Inks and Adhesives" Amoco Chemicals, Bulletin FA-21b, dated Jun. 9, 2001.

(Continued)

*Primary Examiner* — Bijan Ahvazi (74) *Attorney, Agent, or Firm* — Marshall, Gerstein & Borun LLP (57) ABSTRACT

A method of reducing photodegradation of a coenzyme $Q_{10}$ compound when exposed to UV radiation in a composition containing said coenzyme $Q_{10}$ compound comprising combining with said coenzyme $Q_{10}$ compound a compound of formula (I) in an amount effective to quench singlet excited state energy from the coenzyme $Q_{10}$ compound and transfer the singlet excited state energy from the coenzyme $Q_{10}$ compound to the compound of formula (I),

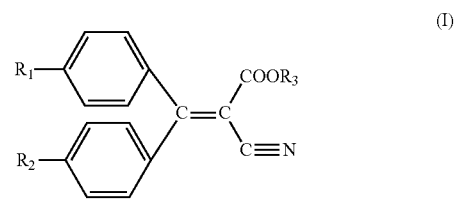

(I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical, thereby photostabilizing the retinoid compound.

12 Claims, 2 Drawing Sheets

U.S. PATENT DOCUMENTS

| | | |
|---|---|---|
| 2003/0176542 A1 | 9/2003 | Abe et al. |
| 2004/0047817 A1 | 3/2004 | Bonda |
| 2004/0047818 A1 | 3/2004 | Bonda |
| 2004/0057914 A1 | 3/2004 | Bonda et al. |
| 2004/0170579 A1 | 9/2004 | Mobius |
| 2004/0247539 A1 | 12/2004 | Wendel et al. |
| 2005/0191249 A1 | 9/2005 | Bonda et al. |
| 2006/0002869 A1 | 1/2006 | Bonda et al. |
| 2006/0008426 A1* | 1/2006 | Doring et al. ............... 424/59 |
| 2006/0062746 A1 | 3/2006 | Brillouet et al. |
| 2006/0228311 A1 | 10/2006 | Bonda et al. |
| 2008/0286217 A1 | 11/2008 | Chaudhuri |
| 2009/0057627 A1 | 3/2009 | Bonda et al. |

FOREIGN PATENT DOCUMENTS

| | | |
|---|---|---|
| EP | 570838 A1 | 11/1993 |
| EP | 0761201 A1 | 3/1997 |
| EP | 1323743 | 7/2003 |
| JP | 08225672 | 9/1996 |
| JP | 20050139263 | 6/2005 |
| SU | 1273360 | 11/1986 |
| WO | WO-00/27337 A2 | 5/2000 |
| WO | WO-02/42368 A2 | 5/2002 |
| WO | WO-2007/128840 A2 | 11/2007 |

OTHER PUBLICATIONS

"Light Absorbing Properties of Naphthalate Containing Polyesters" BP p.l.c., Technical Bulletin N-10, 1991.

Baussard, Jean-Francois, "Chap. II: Donor-Acceptor pairs for Forster Resonance Energy Transfer (FRET):" in Synthesis of New Ionic Functional Polymers by Free Radical Polymerization via the RAFT Process, Dissertation, Catholic University of Louvain, Jan. 26, 2004.

Bonda, "Research Pathways to Photostable Sunscreens," *Cosmetics & Toiletries Magazine*, 123:1, 49-60 (Feb. 5, 2008).

Chatelain et al., "Photostabilization of Butyl Methoxydibenzoylmethane (Avobenzone) and Ethylhexyl Methoxycinnamate by Bis-ethylhexyloxyphenol Methoxyphenyl Triazine (Tinosorb S), a New UV Broadband Filter", Photochemistry and Photobiology, 2003, vol. 74(3): pp. 401-406.

European Search Report for EP 08 10 3204, dated Jul. 17, 2008.

European Search Report for EP 08 10 3205, dated Jul. 25, 2008.

Horiba Jobin Yvon Ltd., *A Guide to Recording Fluorescence Quantum Yields*, www.jyhoriba.co.uk, dated Jun. 3, 2003.

International Search Report for PCT/US2008/058456, dated Jun. 27, 2008.

Katritzky et al., "Synthesis of 3,3-diarylpyrrolidines from Diaryl Ketones", ARKIVOC, Gainesville, FL, United States, 2003, vol. 5, pp. 9-18, Arkat USA Inc. URL: http://arkatusa.org/zark/journal/2003/Bernath/GB-594J/594J.pdf.

Min et al., "Spectroscopic studies on the interaction of cinnamic acid and its hydroxyl derivatives with human serum albumin", *J. Mol. Structure*, 692:71-80 (2004).

Palm, M. D., O'Donoghue, M. N. "Update on Photoprotection" Dermatologic Therapy, vol. 20, pp. 360-376 (2007).

Senchenya et al., "Silicon-containing esters of α-cyanoacrylic acid: synthesis and properties", *Russian Chem. Bul.*, 42:909-911 (1993).

Somsen et. al., "Planar chromatography coupled with spectroscopic techniques" in J. Chromatography A, vol. 703, 613-65 (1995).

Turro et al., *Modern Molecular Photochemistry*, University Science Books (1991).

Written Opinion of the International Searching Authority for PCT/US2008/058456, dated Jun. 27, 2008.

Senchenya, N. G., et al. "Silicon-containing esters of α-cyanoacrylic acid: synthesis and properties" Russian Chem. Bul., vol. 42(5), pp. 909-911 (1993).

* cited by examiner

PHOTOSTABILIZATION OF COENZYME Q COMPOUNDS WITH ALKOXYCRYLENE COMPOUNDS

CROSS-REFERENCE TO RELATED APPLICATION

This application is a divisional of U.S. application Ser. No. 13/294,339, filed Nov. 11, 2011, which is a continuation-in-part of U.S. application Ser. No. 13/282,667, which is a divisional of U.S. application Ser. No. 12/533,598, filed Jul. 31, 2009, which is a continuation-in-part of U.S. Pat. No. 7,588,702, issued Sep. 15, 2009, which is a continuation-in-part of U.S. Pat. No. 7,597,825, issued Oct. 6, 2009. The entire text of the priority application is incorporated herein by reference in its entirety

FIELD OF THE INVENTION

The present invention is directed to compositions and methods to increase the photostability of coenzyme $Q_{10}$ (CAS number 303-98-0) and all other coenzyme compounds, e.g., $Q1$-$Q_{10}$, inclusive, preferably $Q_{10}$. More particularly, the invention relates to the photo stabilization of coenzyme $Q_{10}$ with alkoxycrylene compounds.

BACKGROUND

Coenzyme $Q_{10}$ (structure below, wherein x=10) is an oil soluble compound that is present in virtually all eukaryotic cells. It is found primarily in the mitochondria where it plays a key role in the electron transport chain that generates energy in the form of ATP (adenosine triphosphate), the source of 95% of the energy in the human body. Coenzyme $Q_{10}$, abbreviated as CoQ10 and also known as Ubiquinone, is characterized by the presence of 10 isoprene units on its side chain. Other CoQ compounds with fewer isoprene units exist, e.g., coenzyme $Q_1$ to $Q_9$, but are less common.

Coenzyme Q compounds, wherein x=1-10

This oil-soluble, vitamin-like substance is present in most eukaryotic cells, primarily in the mitochondria. It is a component of the electron transport chain and participates in aerobic cellular respiration, generating energy in the form of ATP. Ninety-five percent of the human body's energy is generated in this way. Therefore, those organs with the highest energy requirements—such as the heart, liver and kidney—have the highest CoQ10 concentrations. There are three redox states of coenzyme Q: fully oxidized (ubiquinone), semiquinone (ubisemiquinone), and fully reduced (ubiquinol). The capacity of this molecule to exist in a completely oxidized form and a completely reduced form enables it to perform its functions in electron transport chain and as an antioxidant respectively. In the reduced forms (ubisemiquinone and ubiquinol) one or both carbonyls (C=O) are replaced by hydroxyl (C—OH) groups.

The antioxidant nature of coenzyme $Q_{10}$ (CoQ10) derives from its energy carrier function. As an energy carrier, the CoQ10 molecule is continually going through an oxidation-reduction cycle. As it accepts electrons, it becomes reduced. As it gives up electrons, it becomes oxidized. In its reduced form, the CoQ10 molecule holds electrons rather loosely, so this reduced CoQ10 molecule will quite easily give up one or both electrons and, thus, act as an antioxidant. CoQ10 inhibits lipid peroxidation by preventing the production of lipid peroxyl radicals ((LLO). Moreover, $CoQH_2$ reduces the initial preferryl radical and singlet oxygen, with concomitant formation of ubisemiquinone and $H_2O_2$. This quenching of the initiating perferryl radicals, which prevent propagation of lipid peroxidation, protects not only lipids, but also proteins from oxidation. In addition, the reduced form of CoQ effectively regenerates vitamin E from the a-tocopheroxyl radical, thereby interfering with the propagation step. Furthermore, during oxidative stress, interaction of $H_2O_2$ with metal ions bound to DNA generates hydroxyl radicals and CoQ efficiently prevents the oxidation of bases, in particular, in mitochondrial DNA. In contrast to other antioxidants, this compound inhibits both the initiation and the propagation of lipid and protein oxidation. It also regenerates other antioxidants such as vitamin E. The circulating CoQ10 in LDL prevents oxidation of LDL, therefore, by providing its benefits in cardiovascular diseases.

CoQ10 is a powerful antioxidant that protects lipids and proteins in the body from oxidation. In its reduced form (ubiquinol) it regenerates vitamin E by reducing the α-tocopheroxyl radical. CoQ10 is added to topically applied skin care creams and lotions for its antioxidant properties and for its reputed ability to improve the appearance of fine lines and wrinkles and maintain the skin's vitality and elasticity.

Coenzyme $Q_{10}$ is approved for use as an orphan product in the treatment of Huntington's disease and mitochondrial cytopathies; other uses include the treatment of congestive heart failure and athletic performance. Coenzyme $Q_{10}$ also helps to maintain a healthy cardiovascular system. There is evidence of CoQ10 deficiency in heart failure. Recently, CoQ10 plasma concentrations have been demonstrated as an independent predictor of mortality in chronic heart failure, CoQ10 deficiency being detrimental to the long-term prognosis of chronic heart failure. CoQ10 is available as medicine in several European countries, but is in these countries also available as a food supplement. Oxidation of the circulating LDL is thought to play a key role in the pathogenesis of atherosclerosis, which is the underlying disorder leading to heart attack and ischemic strokes and CHD. Studies in the last decade have demonstrated that the content of Ubiquinol in human LDL affords protection against the oxidative modifications of LDL themselves, thus lowering their atherogenic potency.

Supplementation of coenzyme $Q_{10}$ has been found to have a beneficial effect on the condition of some sufferers of migraine headaches. CoQ10 is also being investigated as a treatment for cancer, and as relief from cancer treatment side-effects. Another recent study shows a survival benefit after cardiac arrest if coenzyme $Q_{10}$ is administered in addition to commencing active cooling of the body to 90-93 degrees Fahrenheit (32-34 degrees Celsius).

A recent (2007) meta-analysis of the clinical trials CoQ10 for hypertension reviewed all published trials of coenzyme $Q_{10}$ for hypertension, and assessed overall efficacy, consistency of therapeutic action, and side-effect incidence. Coenzyme $Q_{10}$ has been shown to lower systolic blood pressure by up to 17 mm Hg and diastolic blood pressure by up to 10 mm Hg without significant side-effects.

Studies also have shown that diseased gum tissue is deficient in CoQ10 compared to healthy gum tissue. Human clinical trials have shown a link between oral administration of CoQ10 and improved gingival health, immune response in gum tissues, and a reversal of the diseased gum conditions. In addition to oral supplementation, topical application of CoQ10 on gum tissues has been shown to improve periodontitis and gingivitis conditions. A 202 study in 80 Parkinson's disease patients found 1200 mg/day reduced the progression by 44%.

One major drawback to the clinical use of coenzyme $Q_{10}$, especially topically for the uses described above, is the high photodegradation of coenzyme $Q_{10}$ upon exposure to UV light. The absorption of ultraviolet light by coenzyme $Q_{10}$ causes reactions that result in the formation of photoproducts and the reduction of a significant amount of the coenzyme $Q_{10}$ compound. These photoreaction products are the result of UV light causing the excitation of an electron in the coenzyme $Q_{10}$ molecule from an initially occupied, low energy orbital to a higher energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the coenzyme $Q_{10}$ molecule is prone to degrade via a number of known pathways and, reacts to form photoproducts, thereby reducing the remaining therapeutic concentration of coenzyme $Q_{10}$. To photostabilize the coenzyme $Q_{10}$ compound, it must be returned to the ground state before it undergoes the photochemical reactions that forms these photoproducts and, thereby, reduces the concentration of coenzyme $Q_{10}$, thereby reducing its effectiveness for its intended use.

This photoinstability of coenzyme $Q_{10}$ compounds is highly problematic when developing and using topical coenzyme $Q_{10}$ compounds and orally ingested coenzyme $Q_{10}$ compound-containing compositions for clinical purposes. To reduce the amount of photodegradation that occurs in coenzyme $Q_{10}$ compound-containing products, manufacture of the coenzyme $Q_{10}$ product must occur in the dark or under special lighting conditions, and the packaging of the coenzyme $Q_{10}$ product must be light fast. Even if coenzyme $Q_{10}$ compound-containing products are manufactured in the dark and stored in a light fast package, they quickly degrade upon application to the skin, rendering the coenzyme $Q_{10}$ product much less effective.

SUMMARY

The photostabilizing electronic excited state energy has been found to be readily transferred to (accepted by) α-cyanodiphenylacrylate compounds having an alkoxy radical in the four (para) position (hereinafter "alkoxycrylenes") on one of the phenyl rings having the formula (I):

(I)

wherein one of $R_1$ and $R_2$ is a straight or branched chain $C_1$-$C_{30}$ alkoxy radical, preferably $C_1$-$C_8$, more preferably methoxy, and the non-alkoxy radical $R_1$ or $R_2$ is hydrogen; and $R_3$ is a straight or branched chain $C_1$-$C_{30}$ alkyl radical, preferably $C_2$-$C_{20}$.

It has surprisingly been found that the alkoxycrylene compounds of formula (I), described herein, significantly increase the photostability of coenzyme $Q_{10}$ to $Q_{20}$ compounds, such as coenzyme $Q_{10}$, in a composition by 2 to 3-fold.

DETAILED DESCRIPTION OF THE PREFERRED EMBODIMENTS

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical extending from the para position of one or both of the phenyl rings having the formula O—R, wherein R is an alkyl radical, straight chain or branched having 1 to 30 carbon atoms, preferably wherein R=$C_1$ to $C_8$, more preferably $C_2$-$C_{20}$, and most preferably —O—$CH_3$ (methoxy). The oxygen atom of the alkoxy radical is covalently bonded to the para carbon atom of one or both of the phenyl rings, preferably only one of the phenyls, preferably having the formula (II) or (III):

(II)

(III)

wherein $R_3$ is a straight or branched chain $C_1$-$C_{30}$ alkyl radical, preferably $C_2$-$C_{20}$.

The term "crylene" as used herein refers to a chromophoric moiety that includes an α-cyano-β,β-diphenyl propanoic acid ester.

The term "cyano" as used herein refers to a —C≡N group, also designated "—CN."

Topical compositions that contain one or more coenzyme $Q_{10}$ compounds, as described herein, for treating one or more of the human conditions mentioned above, advantageously also may include UV-A and UV-B photoactive compounds in a dermatologically acceptable carrier, optionally including additives, such as emollients, stabilizers, emulsifiers, and combinations thereof. These additives can be used in preparing a UV filter composition, containing one or more coenzyme Q compounds in an emulsion (oil-in-water or water-in-oil) from a composition that includes one or more photoactive compounds and a solvent or a solvent combination that includes one or more organic solvents and water. When made, preferably the emulsion is an oil-in-water (O/W) emulsion, wherein the oil phase is primarily formed from a mixture of the UV filter compound(s) and one or more organic solvents.

The coenzyme Q compound-containing, particularly coenzyme $Q_{10}$ compound-containing compositions advantageously, but optionally, include one or more photoactive compounds, in addition to the coenzyme $Q_{10}$ compound(s), wherein the photoactive compound(s) act to absorb UV radiation. The alkoxycrylene compounds described herein accept electronic singlet excited state energy from coenzyme $Q_{10}$ compounds. The alkoxycrylenes also are very effective UVA absorbers in addition to providing electronic singlet state energy quenching of other UV-absorbing compounds in sunscreen compositions. As described in this assignee's pending application Ser. Nos. 11/891,281 and 12/022,758 filed on Aug. 9, 2007 and Jan. 30, 2008, respectively, the alkoxycrylene molecules described herein are especially effective photo stabilizers when combined with one or more additional electronic singlet excited state quenching compounds such as oxybenzone. Particularly surprising photostabilization is achieved in cosmetic and dermatological compositions containing the alkoxycrylene compounds described herein together with octyl methoxycinnamate and Avobenzone, all of which are optionally useful, alone or in combination with the alkoxycrylene compounds of formula (I) and one or more coenzyme Q compounds, particularly coenzyme $Q_{10}$, as described herein.

In addition to photostabilizing coenzyme Q compounds, the compounds of formula (I) are theorized to also photostabilize the following UV filters contained in coenzyme Q compound-containing compositions, particularly coenzyme $Q_{10}$ compound-containing compositions, including all of the following, including combinations of any two or more, and including compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

The following UV filters, when optionally contained in coenzyme $Q_{10}$ compound-containing compositions should be particularly photostabilized by the alkoxycrylene molecules described herein: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)] aminobenzoate, 2-ethylhexylsalicylate, glycerol p-aminobenzoate, 3,3,5-trimethylcyclohexylsalicylate, and combinations thereof.

The photoactive coenzyme $Q_{10}$ compound-containing compositions, disclosed herein for topical application to skin, can include a variety of additional photoactive compounds, preferably including one or more UV-A photoactive compounds and one or more UV-B photoactive compounds. Preferably, a coenzyme $Q_{10}$ compound-containing composition also includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

UV A radiation (about 320 nm to about 400 nm), is recognized as contributing to causing damage to skin, particularly to very lightly colored or sensitive skin. A coenzyme $Q_{10}$ compound-containing sunscreen composition preferably includes a UV-A photoactive compound. Preferably, a coenzyme $Q_{10}$ compound-containing sunscreen composition includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. In one embodiment of the coenzyme $Q_{10}$ compound-containing compositions described herein, one or more of a highly polar solvent is present in the oil-phase of the composition. Preferably, a sufficient amount of a polar solvent is present in the coenzyme $Q_{10}$ compound-containing topical compositions to raise the dielectric constant of the oil-phase of the composition to a dielectric constant of at least about 7, preferably at least about 8.

It has surprisingly been found that the alkoxycrylene compounds of formula (I) described herein unexpectedly and significantly increase the photostability of a coenzyme Q compound, particularly a coenzyme $Q_{10}$ compound, in a composition by about 2 to 3-fold. The ability of the alkoxycrylene compounds to stabilize coenzyme $Q_{10}$ compounds is theorized to be concentration dependent, with the amount of coenzyme $Q_{10}$ compound photostabilization increasing with the concentration of the alkoxycrylene compound. For example, the percentages of coenzyme $Q_{10}$ lost in compositions exposed to UV radiation comprising with and without 5% ethylhexyl methoxycrylene were 27.4% lost with 5% ethylhexyl methoxycrylene vs. 64.46% lost without the ethylhexyl methoxycrylene.

In accordance with one important topical composition embodiment, an alkoxycrylene compound of formula (I) is combined in a dermatological composition with a coenzyme $Q_{10}$ compound. The group of coenzyme $Q_{10}$ compounds advantageous according to this embodiment of the invention is defined as including all dermatologically and/or pharmaceutically acceptable coenzyme $Q_{10}$ compounds, including $Q_1$ to $Q_{10}$ and all of their partially or fully oxidized and partially or fully reduced forms.

The total amount of the coenzyme $Q_{10}$ compound in the finished coenzyme $Q_{10}$ compound-containing composition is chosen from about 0.01% by weight to about 5% by weight, preferably from about 0.05% by weight to about 2% by weight, more preferably from about 0.01% by weight to about 1.0% by weight, and most preferably about 0.1% to about 0.5%, in each case based on the total weight of the composition.

The alkoxycrylene compound is a compound of formula (I):

wherein one of $R_1$ and $R_2$ is a straight or branched chain $C_1$-$C_{12}$ alkoxy radical, and the non-alkoxy $R_1$ or $R_2$ is hydrogen and $R_3$ is a straight or branched chain $C_1$-$C_{24}$ alkyl radical. In a specific embodiment, the compound of formula (I) is ethylhexyl methoxycrylene (EHMC, IV).

In another specific embodiment, the compound of formula (I) is butyloctyl methoxycrylene (BOMeOC, V).

The total amount of the alkoxycrylene compound in the finished coenzyme $Q_{10}$ compound-containing composition is chosen from the range of about 0.01% by weight to about 20% by weight, preferably from about 0.1 to about 10% by weight, for example from about 0.1% to about 5% by weight, in each case based on the total weight of the composition.

The molar ratio of the alkoxycrylene compound (formula (I)) to the coenzyme $Q_{10}$ compound in the finished coenzyme $Q_{10}$ compound-containing composition is from about 1 to 1 to about 40 to 1. Typically, about 1 to 5 wt. % of Ethylhexyl methoxycrylene (compound of formula (I)) is used to photostabilize 0.1 to 0.5 wt. % coenzyme $Q_{10}$. Accordingly, the preferred range molar ratios of the alkoxycrylene compound to coenzyme $Q_{10}$ compound is about 10 to 1 to about 55 to 1.

The coenzyme $Q_{10}$ compound-containing compositions according to the invention can comprise cosmetic auxiliaries such as those conventionally used in such compositions, e.g. preservatives, bactericides, perfumes, antifoams, dyes, pigments which have a coloring effect, thickeners, moisturizers and/or humectants, fats, oils, waxes or other conventional constituents of a cosmetic or dermatological composition, such as alcohols, polyols, polymers, foam stabilizers, electrolytes, organic solvents or silicone derivatives.

Particularly advantageous coenzyme $Q_{10}$ compound-containing compositions are also obtained when other antioxidants are used as additives or active ingredients. According to this embodiment of the invention, the coenzyme $Q_{10}$ compound-containing compositions advantageously comprise one or more additional antioxidants. Favorable, but nevertheless optional antioxidants which may be used are all antioxidants customary or suitable for cosmetic and/or dermatological applications.

The additional content of antioxidants may also be included in the topically applied compositions. According to this embodiment, favorable antioxidants which can be used together with one or more coenzyme $Q_{10}$ compounds are any antioxidants suitable or conventional for topical cosmetic and/or dermatological applications.

The optional additional antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. .alpha.-carotene, .beta.-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to .mu.mol/kg), and also (metal) chelating agents (e.g. .alpha.-hydroxy fatty acids, palmitic acid, phytic acid, lactoferrin), .alpha.-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. .gamma.-linolenic acid, linoleic acid, oleic acid), folic acid and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, .alpha.-glycosylrutin, ferulic acid, furfurylideneglucitol, carnosine, butylhydroxytoluene, butylhydroxyanisole, nordihydroguaiaretic acid, trihydroxybutyro-phenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention. Excellent results have been shown with an addition of both butyl hydroxy toluene at 0.01% to 0.5%, e.g., about 0.08%, and tocophenol at about 0.1% to about 0.5%, e.g., about 0.28%, based on the total weight of the composition.

The amount of additional antioxidants (one or more compounds) in the compositions is preferably about 0.001 to about 20% by weight, particularly preferably about 0.05 to about 10% by weight, in particular about 0.1 to about 10% by weight, based on the total weight of the composition.

If vitamin E and/or derivatives thereof are the antioxidant or antioxidants, it is advantageous to choose their respective concentrations from the range from about 0.001 to about 10% by weight, based on the total weight of the composition.

In accordance with another embodiment, the coenzyme $Q_{10}$ compound-containing compositions containing an alkoxycrylene compound of formula (I) according to the invention are combined with hydrophilic skincare active ingredients and/or a broad-band filter compound and optionally, but preferably, together with a dibenzoylmethane derivative.

In another embodiment, advantageous hydrophilic active ingredients also may be added to the topically applied compositions. These hydrophilic compounds (individually or in any combinations with one another) are stabilized by their use together with an alkoxycrylene in a coenzyme $Q_{10}$ compound-containing composition, according to this embodiment, include those listed below:

biotin; carnitine and derivatives; creatine and derivatives; folic acid; pyridoxine; niacinamide; polyphenols (in particular flavonoids, very particularly alpha-glucosylrutin); ascorbic acid and derivatives; Hamamelis; Aloe Vera; panthenol; amino acids.

Particularly advantageous hydrophilic active ingredients for the purposes of this embodiment are water-soluble antioxidants, such as, for example, vitamins.

The amount of hydrophilic active ingredients (one or more compounds) in the coenzyme $Q_{10}$ compound-containing compositions is preferably about 0.0001 to about 10% by weight, particularly preferably about 0.001 to about 5% by weight, based on the total weight of the composition.

It is particularly advantageous when the coenzyme $Q_{10}$ compound-containing compositions according to the present invention comprise anti-acne, anti-aging, wrinkle reducing, cosmetic or dermatological active ingredients, such as one or more retinoid compounds.

Advantageous further active ingredients that are optionally included in topically-applied compositions include natural active ingredients and/or derivatives thereof, such as e.g. retinol, carotenoids, creatine, taurine and/or beta.-alanine.

Coenzyme $Q_{10}$ compound-containing compositions may include known antiwrinkle active ingredients, such as flavone glycosides (in particular .alpha.-glycosylrutin), a retinoid, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

In accordance with still another important embodiment, an alkoxycrylene compound of formula (I) is combined in a coenzyme $Q_{10}$ compound-containing anti-acne, anti-aging, wrinkle reducing, sunscreen or dermatological composition with particulate UV filter substances and/or a broad-band filter compound and optionally, but preferably, together with a dibenzoylmethane derivative and/or a dialkyl naphthalate UV filter compound.

Preferred particulate UV filter substances for the purposes of this embodiment of the present invention are inorganic pigments, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of this embodiment may also be used in the form of commercially available oily or aqueous predispersions. Zinc oxide particles and predispersions of zinc oxide particles which are suitable according to the invention are distinguished by a primary particle size of <300 nm and can be obtained under the following proprietary names from the stated companies:

| Proprietary name | Coating | Manufacturer |
| --- | --- | --- |
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (> = 56%)/Ethylhexyl Hydroxystearate Benzoate/ Dimethicone/Cyclomethicone | Collaborative Laboratories |
| Samt-UFZO-450/D5 (60%) | ZnO (60%)/Cyclomethicone/ Dimethicone | Miyoshi Kasei |

Particularly preferred zinc oxides for the purposes of this embodiment are Z-Cote HP1 and Z-Cote from BASF and zinc oxide NDM from Haarmann & Reimer.

Titanium dioxide pigments useful in this embodiment may be in the form of both the rutile and anatase crystal modification and may for the purposes of the present invention advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the particulate sunscreen additive embodiment may consist of aluminum oxide ($Al_2O_3$), aluminum hydroxide $Al(OH)_3$ or aluminum oxide hydrate (also: alumina, CAS No.: 1333-84-2), sodium hexametaphosphate ($NaPO_3$)$_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the particulate sunscreen additive embodiment may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) or alginic acid. These organic surface coatings may occur alone, in combination and/or in combination with inorganic coating materials.

Coated and uncoated titanium dioxides of the particulate sunscreen additive embodiment may be used in the form of commercially available oily or aqueous predispersions. It may be advantageous to add dispersion aids and/or solubilization mediators.

The coenzyme $Q_{10}$ compound-containing anti-acne, anti-aging, wrinkle reducing, cosmetic or dermatological compositions described herein may include conventional additives, solvents, and water concentrations when used for anti-acne, anti-aging, wrinkle reducing, cosmetic or dermatological treatment, care and cleansing of skin and/or the hair and as a make-up product in decorative cosmetics.

In accordance with another important embodiment, an alkoxycrylene compound of formula (I) is combined in a coenzyme $Q_{10}$ compound-containing anti-acne, anti-aging, wrinkle reducing, sunscreen or dermatological composition with a lipophilic oxidation or UV-sensitive active ingredients and/or a broad-band filter compound and optionally, but preferably, together with a dibenzoylmethane derivative.

Advantageous lipophilic active ingredients which are stabilized in an excellent manner when used with the alkoxycrylenes described herein by the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{C_{n-octanol}}{C_{water}}$$

It is advantageous to choose the lipophilic active ingredients from the group of plastoquinones. For the purposes of the present invention, coenzyme $Q_{10}$, is an excellent lipophilic compound, having a log P value of about 15.

Further lipophilic acid ingredients advantageous according to this embodiment of the invention are carotenoids. For the purposes of the present invention, beta.-carotene, which has a log P value of 15, for example, is particularly advantageous.

Further lipophilic active ingredients advantageous according to this embodiment of the invention are: lipoic acid and derivatives, vitamin E and derivatives, vitamin F, dioic acid [8-hexadecene-1,16-dicarboxylic acid (CAS number 20701-68-2)]

The amount of lipophilic active ingredients (one or more compounds) in the compositions, in addition to coenzyme $Q_{10}$, is preferably about 0.0001 to about 10% by weight, particularly preferably about 0.001 to about 5% by weight, based on the total weight of the composition.

EXAMPLES

To test the effects of simulated solar UV radiation on Coenzyme $Q_{10}$ (Ubiquinone), two test formulations were prepared, each containing 0.1% coenzyme $Q_{10}$. One formulation contained no photostabilizer, the other contained 5% Ethylhexyl methoxycrylene (Formula (I)). The compositions of the two formulations and the preparative procedure can be found in Table 1.

TABLE 1

Test formulations and preparative procedure

| | | No coenzyme $Q_{10}$ | 0.1% coenzyme $Q_{10}$ | |
|---|---|---|---|---|
| | Ingredients | | no photo-stabilizer | with 5.0% Ethylhexyl methoxycrylene |
| | Oil Phase | | | |
| 1 | Isopropyl Myristate | 4.00 | | |
| 1b | Ethylhexyl methoxycrylene | | | 5.00 |
| 2 | Caprylic/capric triglycerides | 5.00 | 5.00 | 5.00 |
| 3 | Isopropyl Myristate | 5.00 | 5.00 | 5.00 |
| 4 | Cetearyl Alcohol | 0.50 | 0.50 | 0.50 |
| 7 | Butylated hydroxy toluene | 0.08 | 0.08 | 0.08 |
| 8 | α Tocopherol | 0.28 | 0.28 | 0.28 |
| 9 | Coenzyme $Q_{10}$ | | 0.10 | 0.10 |
| | Emulsifiers | | | |
| 5 | Glyceryl Stearate, PEG-100 Stearate | 4.00 | 4.00 | 4.00 |
| 6 | Glyceryl Stearate | 0.02 | | 0.05 |
| | Water Phase | | | |
| 10 | Water | 75.47 | | 74.44 |
| 11 | Disodium EDTA | 0.05 | | 0.05 |
| 12 | Carbomer | 0.25 | | 0.25 |
| 13 | Propylene Glycol | 4.00 | | 4.00 |
| 14 | Caprylyl Glycol, Phenoxyethanol, Hexylene glycol | 1.00 | | 0.50 |
| 15 | Triethanolamine | 0.25 | | 0.25 |
| | Total | 100.00 | | 100.00 |

Preparative procedure: 1. Charge a secondary vessel with ingredients 1-3. Heat to 65 degrees C. Add ingredients 4-6 and stir until homogeneous and clear. Stop heating and add ingredients 7-9 with mixing right before combining with water phase.

2. Charge main vessel with ingredient 10. Dissolve ingredient 11. Add ingredient 12 and stir until fully incorporated.

3. Heat water phase ingredients 10-12 to 65 degrees C. Add premix of ingredients 13-15 into ingredients 10-12.

4. Add oil phase (ingredients 1-9) to water phase (ingredients 10-12) with stirring and stop heating.

5. Homogenize until batch reaches 55° C., and then resume sweep mixing while cooling.

6. Q.S. water to replace water lost during processing.

A sample of each test formulation was analyzed by HPLC for Coenzyme $Q_{10}$ (CoQ10) content before and after exposure to simulated solar radiation. Radiation was supplied by a Q-Sun Xe-1 xenon test chamber equipped with a Daylight B/B filter and a chiller unit to maintain temperature in the chamber below 30° C. Chromatographic analyses were performed on a Hewlett Packard Series 1100 HPLC System equipped with quaternary pumps, a vacuum degasser, an auto-injector, and a dynamic absorbance detector (DAD), connected to a computer running Chemstation for LC 3D (Agilent Technologies). Following are the conditions used for the chromatographic analyses of CoQ10 content in a topical lotion for contact against the skin:

Reagents:
1. Acetonitrile, HPLC grade
2. Tetrahydrofuran (THF), HPLC grade
3. Methanol, HPLC grade
4. Water, HPLC grade Preparation of Mobile Phase A and Mobile Phase B:

Mobile Phase A—10% THF in Acetonitrile was prepared by pipetting 50 ml THF into about 400 ml Acetonitrile in a 500 ml volumetric flask, mixing and bringing to volume with Acetonitrile.

Mobile Phase B—1% Methanol in water was prepared by pipetting 10 ml Methanol into about 950 ml water in a 1 L volumetric flask, mixing and bringing to volume with water.

B. Conditions

| | |
|---|---|
| Column: | Luna 5μ, C8 (2) 100A, 150 * 4.6 mm |
| Mobile Phase (A): | 10% THF in Acetonitrile |
| Mobile Phase (B): | 1% Methanol in water |
| Flow Rate: | 1.0 ml/min |
| Temperature: | 450° C. |
| Detector: | UV Spectrophotometer @280 nm |
| Injection: | 8 μl |

Pump Program

| Time (min) | Mobile Phase A | Mobile Phase B |
|---|---|---|
| 0.0 | 92.0 | 8.0 |
| 2.0 | 92.0 | 8.0 |
| 4.5 | 99.8 | 0.2 |
| 18.0 | 99.8 | 0.2 |
| 22.0 (stop) | 92.0 | 8.0 |

The Sample Preparation and Procedure was performed under low light conditions.

Pre-Irradiated and Control Samples:

Weigh about 0.2 grams of the test material to a 5 cm×5 cm roughened quartz plate (roughness=6 μm). Spread the test material evenly and keep the plate in dark for one hour.

Irradiated Samples:

Apply approximately 0.2 grams of the test material to a 5 cm×5 cm roughened quartz plate. Spread the test material evenly. Irradiate the plate in the xenon test chamber with 15 W/m2 TUV for one hour. 15 W/m2 for one hour is approximately equal to a 2 minimal erythemal dose (MED) of direct sunlight. TUV is total irradiance between 300 to 400 nm.

Sample Extraction:

Add about 2 ml THF to rinse the sample from the plate twice. Mix well and filter through PTFE sample filters. Analyze by HPLC according to the method described above.

Calculation of Coenzyme $Q_{10}$ Content:

Calculate CoQ10 content using Tocopherol, included in the test formulations as an internal standard, by comparing the ratio of the areas of the Tocopherol and Coenzyme $Q_{10}$ peaks before and after irradiation.

Results:

For the formulation containing 1% CoQ10 and no photostabilizer, Tocopherol eluted at 7.324 minutes (pre-irradiation) or 7.241 minutes (post-irradiation), and CoQ10 eluted at 15.634 minutes (pre-irradiation) and 15.415 minutes (post-irradiation). The ratio of the area of the Tocopherol peak to the area of the CoQ10 peak was 0.8553 before irradiation and 2.4072 after irradiation. This calculates to a loss of CoQ10 of 64.47%.

For the formulation containing 1% CoQ10 and 5% Ethylhexyl methoxycrylene, Tocopherol eluted at 7.652 minutes (pre-irradiation) and 7.696 minutes (post-irradiation), and CoQ10 eluted at 19.953 minutes (pre-irradiation) and at 19.904 minutes (post-irradiation). The ratio of the area of the Tocopherol peak to the area of the CoQ10 peak was 0.8328 before irradiation and 1.1471 after irradiation. This calculates to a loss of CoQ10 of 27.40%.

Figure 1:
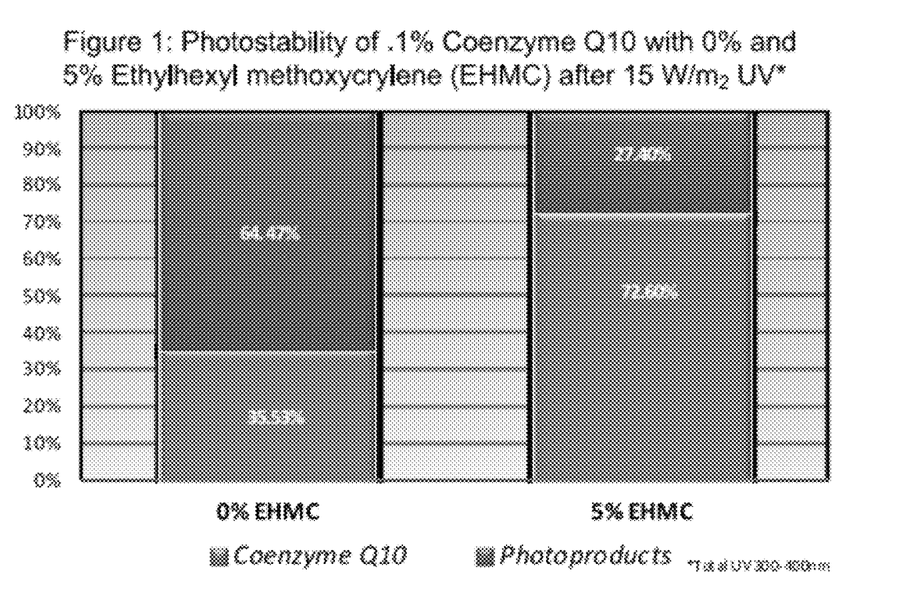
FIG. 1 is a bar graph showing the amount of enzyme $Q_{10}$ lost (upper portion of bars) and retained (lower portion) via photodegradation when test formulations, with and without 5% formula (I) compound, were irradiated with approximately a 2 minimal erythemal dose (MED) of direct sunlight.

Therefore, after exposure to 2 MED, the photostabilized CoQ10 formulation retains over twice as much CoQ10 compared to the unstabilized formulation, and photoproducts are reduced by 57.5%, the results are displayed graphically in FIG. 1.

Figure 2:
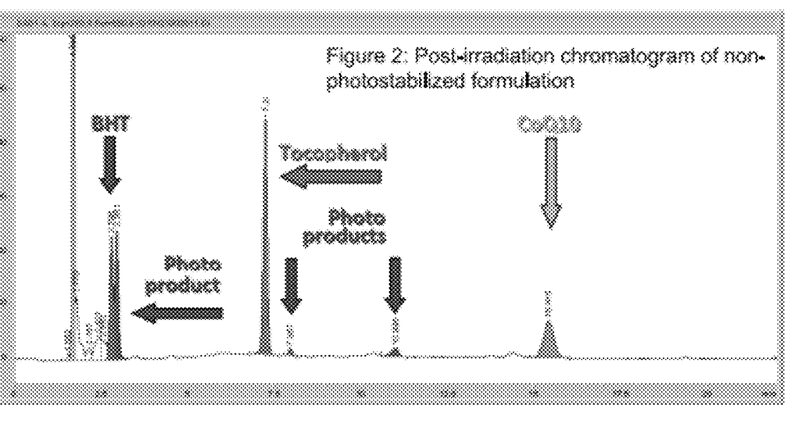
FIGS. 2 and 3 are post-irradiation chromatograms of the test formulations tested for photodegredation, as shown in FIG. 1, showing photoproduct peaks for coenzyme $Q_{10}$ and compounds resulting from photodegredation.
Figure 3:
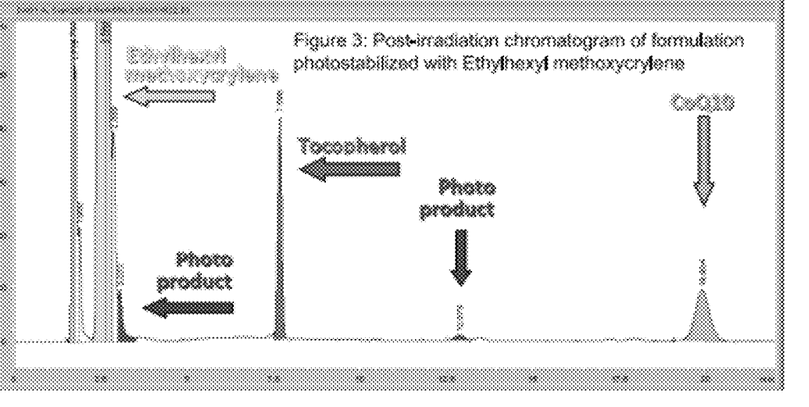

Several new peaks appeared on the HPLC chromatograms taken after the samples were exposed to simulated sunlight. These new peaks are attributed to photoproducts resulting from the photodegradation of the Coenzyme $Q_{10}$. The locations of these new peaks are depicted in FIG. 2 and FIG. 3, which display the chromatograms taken after irradiation of the formulations containing no photostabilizer (FIG. 2) and 5% Ethylhexyl methoxycrylene (FIG. 3) respectively. One can see that photoproducts are much less prevalent in the chromatogram taken of the photostabilized formulation.

Conclusions: Coenzyme $Q_{10}$ is highly sensitive to UV radiation. When incorporated into a skin care lotion that is applied to a substrate and exposed to a low dose of simulated solar radiation, CoQ10 experiences rapid degradation and production of photoproducts. Incorporation of the photostabilizer Ethylhexyl methoxycrylene in a formulation containing CoQ10 greatly improves its preservation from photodegradation, more than doubling the amount that is retained after UV exposure and, presumably, that would be bioavailable to the skin.

The invention claimed is:

1. A photostabilized sunscreen cosmetic or dermatological composition comprising a coenzyme $Q_{10}$ compound in an amount of about 0.001% to about 5% by weight and a compound of formula (I) in an amount of about 0.01% to about 20% by weight, based on the total weight of the composition, wherein the compound of formula (I) is (I)

wherein one of $R_1$ and $R_2$ is a straight or branched chain $C_1$-$C_{30}$ alkoxy radical, and the non-alkoxy $R_1$ or $R_2$ is hydrogen; and $R_3$ is a straight or branched chain $C_1$-$C_{30}$ alkyl radical.

2. The photostabilized composition of claim 1, wherein $R_1$ is methoxy and $R_2$ is hydrogen.

3. The photostabilized composition of claim 1, wherein $R_1$ is hydrogen and $R_2$ is methoxy.

4. The photostabilized composition of claim 1, wherein $R_3$ is a $C_{12}$-$C_{24}$ straight chain or branched alkyl.

5. The photostabilized composition of claim 4, wherein $R_3$ is a 2-butyloctyl radical.

6. The photostabilized composition of claim 4, wherein $R_3$ is an 2-ethylhexyl radical.

7. The photostabilized composition of claim 1, wherein the compound of formula (I) is present in an amount in the weight range of about 0.1% to about 20%, based on the total weight of the composition.

8. The photostabilized composition of claim 7, wherein the compound of formula (I) is present in an amount in this weight range of about 0.1% to about 10%, based on the total weight of the composition.

9. The photostabilized composition of claim 1, wherein the compound of formula (I) is present in an amount in this weight range of about 0.1% to about 5%, based on the total weight of the composition.

10. The photostabilized composition of claim 1, wherein the coenzyme $Q_{10}$ compound is present in an amount in the weight range of about 0.01% to about 5%, based on the total weight of the composition.

11. The photostabilized composition of claim 10, wherein the coenzyme $Q_{10}$ compound is present in this weight range of about 0.01% to about 1%, based on the total weight of the composition.

12. The photostabilized composition of claim 11, wherein the coenzyme $Q_{10}$ compound is present in this weight range of about 0.01% to about 0.5%, based on the total weight of the composition.

* * * * *